United States Patent [19]

Yamada

[11] Patent Number: 5,030,382
[45] Date of Patent: Jul. 9, 1991

[54] PYRIMIDINE DERIVATIVES

[75] Inventor: Shuhei Yamada, Suwa, Japan

[73] Assignee: Seiko Epson Corporation, Tokyo, Japan

[21] Appl. No.: 498,198

[22] Filed: Mar. 23, 1990

[30] Foreign Application Priority Data

Mar. 30, 1989 [JP] Japan .................................. 1-79034
Jul. 5, 1989 [JP] Japan ................................. 1-173511

[51] Int. Cl.$^5$ ..................... C09K 19/34; C07D 239/00
[52] U.S. Cl. .......................... 252/299.61; 252/299.01; 544/245
[58] Field of Search ....................... 252/299.01, 299.61, 252/299.62, 299.63, 299.65, 299.66; 350/350 R, 350 S; 544/242, 245, 298, 315, 316, 318, 335

[56] References Cited

U.S. PATENT DOCUMENTS 4,551,264 11/1985 Eidenschink et al. .......... 252/299.62
4,820,839 4/1989 Kranse et al. ...................... 544/316

FOREIGN PATENT DOCUMENTS 63216858 9/1989 Japan .

*Primary Examiner*—John S. Maples
*Assistant Examiner*—Shean C. Wu
*Attorney, Agent, or Firm*—Blum Kaplan

[57] ABSTRACT 2-(3',5'-difluoro-4'-cyanophenyl)pyrimidine derivatives represented by the general formula:

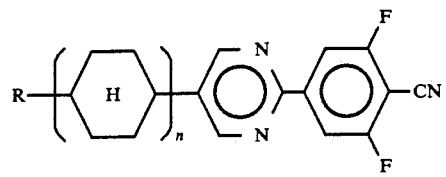

wherein R is a straight chain alkyl having 1 to 10 carbon atoms, n is 0 or 1, the cyclohexane ring is the trans isomer, exhibiting the nematic phase and having a low threshold voltage. The difluorocyanophenyl pyrimidine derivatives may be included in liquid crystal compositions for improved display devices having a low threshold voltage and a low driving voltage.

14 Claims, No Drawings

PYRIMIDINE DERIVATIVES

BACKGROUND OF THE INVENTION

This invention relates to 2-(3',5'-difluoro-4'-cyanophenyl)pyrimidine derivatives, and more particularly to novel liquid crystal compositions including 2-(3',5'-difluoro-4'cyanophenyl)pyrimidine derivatives suitable for use in electro-optical displays.

Liquid crystal display devices utilize electro-optical effects possessed by liquid crystals. The liquid crystal materials used in these devices have a nematic phase, a cholesteric phase and a smectic phase. The most widely used display system uses liquid crystal materials in a twisted nematic mode.

Liquid crystal display devices have several advantages. The devices are small in size and can be made thin, and can be driven at low voltage with low power consumption. The liquid crystal material is a light receiving element so that when a liquid crystal display is viewed over a long time, eye strain does not occur.

In view of these advantages, liquid crystal display technology has been applied to watches, cameras, electronic counters, audio equipment, automobile dashboard indicators, telephone equipment, measuring devices, and the like. More particularly, liquid crystal display devices are also used presently in personal computers and word processor displays and in other devices including displays which require high resolution and many pixels, including black and white and color pocket televisions, and the like. Thus, liquid crystal display devices continue to attract attention as potentially replacing cathode ray tubes. As a result, liquid crystal display devices are widely used in various areas and it is likely that their use will be broadened further.

For practical use, liquid crystal compositions must possess the following characteristics.
1. The liquid crystal materials must be colorless and thermally, optically, electrically and chemically stable;
2. Have a wide nematic temperature range;
3. A rapid electro-optical response speed;
4. Require a low driving voltage;
5. A steep rise in voltage-light transmittance;
6. The temperature dependency of threshold voltage be small; and
7. A wide visual angle.

Many liquid crystal materials possess the first of the above-desired properties, however, no single compound satisfies all of the remaining characteristics. Thus, liquid crystal compositions are formed of several different nematic liquid crystal compounds or liquid crystal compositions are obtained by mixing liquid crystal compounds with non-liquid crystal compounds to obtain the desirable properties.

In order to decrease the driving voltage of a liquid crystal display device, it is necessary to reduce the threshold voltage. However, the following relationship exist between threshold voltage ($V_{th}$), the elasticity constant (K) and dielectric constant anisotropy ($\Delta\epsilon$):

$$V_{th} \propto (K/\Delta\epsilon)^{\frac{1}{2}}.$$

Thus, in order to decrease $V_{th}$, a liquid crystal compound having large $\Delta\epsilon$ and K is required.

Accordingly, it is desirable to provide an improved liquid crystal material having a low threshold voltage and overcomes disadvantages in present liquid crystal compositions.

SUMMARY OF THE INVENTION

Generally speaking, in accordance with the invention, compounds having a pyrimidine skeleton with cyano and fluoro groups are provided. The 2-(3',5'-difluoro-4'-cyanophenyl)pyrimidine derivatives are represented by the general formula:

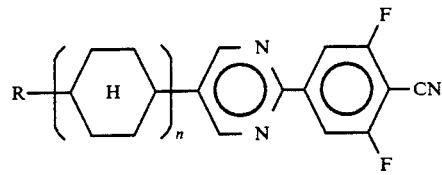

wherein R is a straight chain alkyl having 1 to 10 carbon atoms, n is 0 or 1 and the cyclohexane ring is the trans isomer. The pyrimidine derivatives may be included in a twisted nematic liquid crystal compositions include to reduce the driving voltage.

Accordingly, it is an object to provide improved liquid crystal compounds.

It is another object of the invention to provide 2-(3',5'-difluoro-4'-cyanophenyl) pyrimidine derivatives.

It is a further object of the invention to provide 2-(3',5'-difluoro-4'-cyanophenyl)pyrimidine derivatives having a low driving voltage.

Still another object of the invention is to provide 2(3',5'-difluoro-4'-cyanophenyl) pyrimidine derivatives suitable for use in liquid crystal compositions for electro-optical display devices.

Still a further object of the invention is to provide a method for preparing improved 2-(3',5'-difluoro-4'-cyanophenyl) pyrimidine derivatives.

Yet a further object of the invention is to provide improved liquid crystal display devices including liquid crystal compositions including 2-(3',5'-difluoro-4'-cyanophenyl)pyrimidine derivatives.

Yet another object of the invention is to provide improved liquid crystal compositions including 2-(3',5'-difluoro-4'cyanophenyl)pyrimidine derivatives to be used in large capacity liquid crystal displays.

Still other objects and advantages of the invention will in part be obvious and will in part be apparent from the specification.

The invention accordingly comprises the several steps and the relation of one or more of such steps with respect to each of the others thereof, which will be exemplified in the composition, method and device hereinafter disclosed, and the scope of the invention will be indicated in the claims.

DESCRIPTION OF THE PREFERRED EMBODIMENTS

The pyrimidine skeleton with cyano group and fluoro group compounds prepared in accordance with the invention are 2-(3',5'difluoro-4'-cyanophenyl) pyrimidine derivatives represented by the general formula:

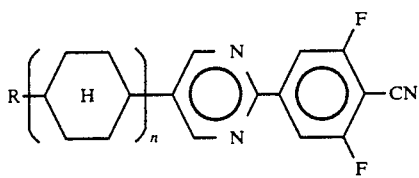
[I]
wherein R is a straight chain alkyl having 1 to 10 carbon atoms, n is 0 or 1 and the cyclohexane ring is the trans isomer. Preferably, the number of carbon atoms in R is between about 2 and 5.
The 2-(3',5'-difluoro-4'-cyanophenyl) pyrimidine derivatives can be produced by the following Reaction Scheme I:
REACTION SCHEME I
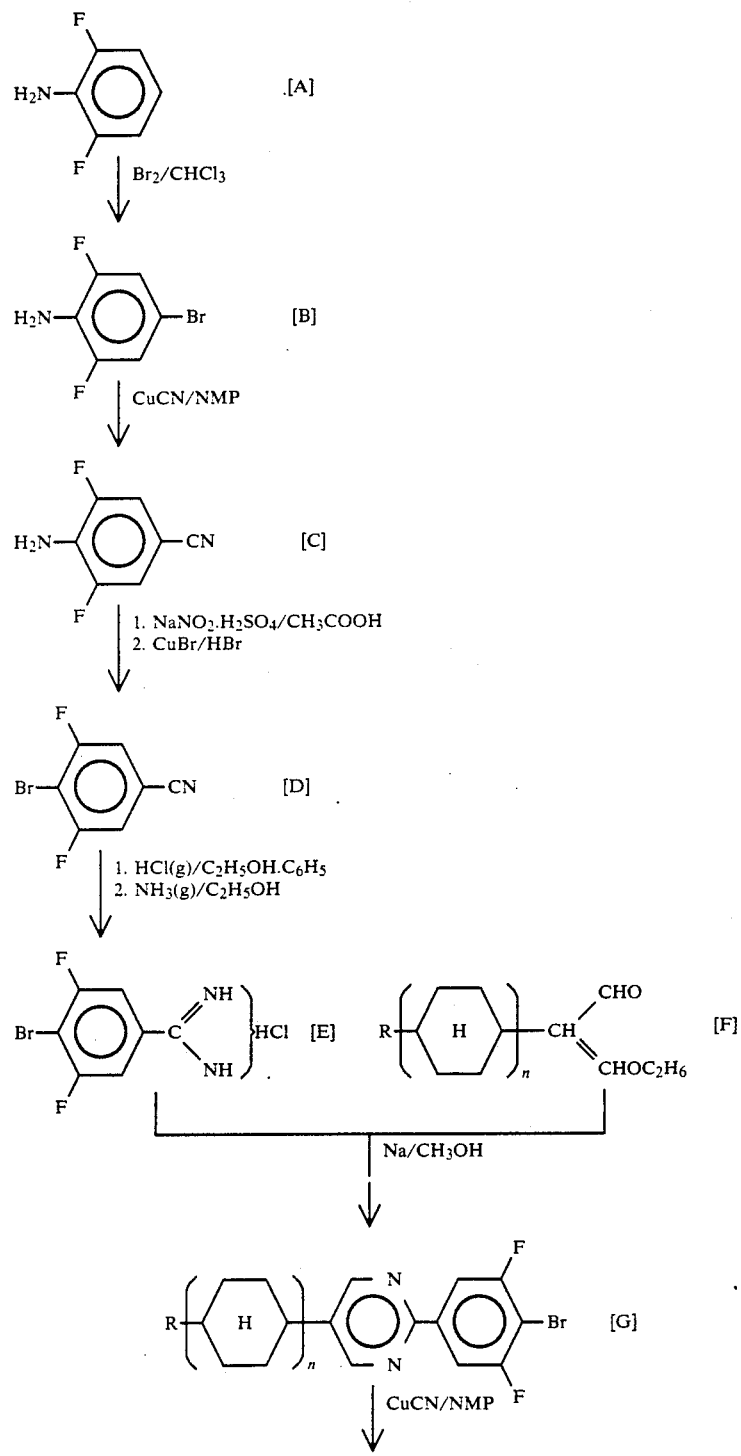

REACTION SCHEME I
-continued

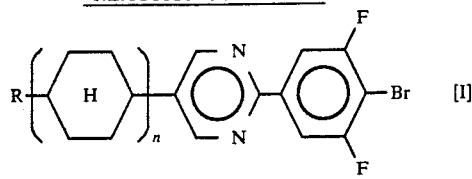

In the method of preparation, Compound [A], 2,6-difluoroaniline, is reacted with bromine in chloroform to yield compound [B], 4-bromo-2,6-difluoroaniline. Compound [B] is mixed with copper (I) cyanide in N-methylpyrrolidone to yield compound [C], 4-cyano-2,6-difluoroaniline. Compound [C] is mixed with sodium nitrite and sulfuric acid in acetic acid to yield a diazonium salt. The diazonium salt is mixed with copper (I) bromide in hydrobromic acid to yield compound [D], 5-cyano-1,3-difluorobenzene.

Compound [D] is mixed with anhydrous hydrogen chloride gas in a solvent mixture of ethanol and benzene. The solvent mixture is distilled off and the resultant crystals are reacted with anhydrous ammonia gas in ethanol to yield compound [E], 4-bromo-3,5-difluorobenzamidine hydrogen chloride. Compound [E] and a 3-ethoxy acrolein compound [F] are mixed in ethanol with metallic sodium to yield compound [G], a 2-(3',5'-difluoro-4'-bromophenyl) pyrimidine. Compound [G] is mixed with copper (I) cyanide in N-methylpyrrolidone to yield a novel liquid crystal compound in accordance with the invention.

The following Examples are set forth by way of illustration to show preparation of the pyrimidine derivatives in accordance with the invention. They are set forth for purposes of illustration only, and are not intended in a limiting sense.

EXAMPLE 1

Preparation of 2-(3',5'-difluoro-4'-cyanophenyl)-5pentylpyrimidine.

Step 1:

300 g of bromine was added drop-wise to 231 g of 2,6-difluoroaniline dissolved in 400 ml of chloroform. The mixture was refluxed for one hour and the reaction solution was poured into an aqueous 10% solution of potassium hydroxide. The potassium hydroxide was extracted with chloroform and the organic layer was washed with an aqueous 10% solution of potassium hydroxide and water. The chloroform was distilled off and the residue was distilled under reduced pressure (bp: 70°−80° C./4 mmHg) and recrystallized from hexane, to yield 292 g of 4-bromo-2,6-difluoroaniline.

Step 2:

132 g of 4-bromo-2,6-difluoroaniline, 70 g of copper (I) cyanide and 444 ml of N-methylpyrrolidone were mixed in a flask and refluxed for 3 hours. The reaction solution was poured into a solution including 266 g of iron (III) chloride, 85 ml of concentrated hydrochloric acid and 315 ml of water. The solution was extracted with chloroform and washed with water and an aqueous 10% solution of potassium hydroxide. The chloroform was distilled off. The residue was distillated under a reduced pressure (bp: 90°−110° C./4 mmHg) and recrystallized from a solvent mixture of hexane and chloroform, to yield 56 g of 4-cyano-2,6-difluoroaniline.

Step 3:

24 g of sodium nitrite was added to 180 ml of concentrated sulfuric acid cooled to a temperature of at least 10° C. 38 ml of acetic acid was added to the mixture. 53 g of 4-cyano-2,6difluoroaniline was added gradually to keep the temperature of the solution between about 20° and 25° C. The mixture was stirred at 20°−25° C. for one hour. A solution was prepared by dissolving 60 g of copper (I) bromide in 180 ml of an aqueous 48% solution of hydrobromic acid. The mixture was added dropwise to the solution and the solution was stirred at room temperature for 15 hours. Water was added to the solution, and the solution was extracted with chloroform and washed with water. The chloroform in the aqueous layer was distilled off and the residue was recrystallized from a solution mixture of methanol and acetone, to yield 25 g of 2-bromo-5-cyano-1,3-difluorobenzene.

Step 4:

25 g of 2-bromo-5-cyano-1,3-difluorobenzene was dissolved in a solvent mixture of 48 ml of ethanol and 165 ml of benzene and cooled to at least 0° C. Anhydrous hydrogen chloride gas was absorbed for one hour. The solvent was distilled off and the residual crystals were washed with ether. The crystals were added to 48 ml of ethanol, and the solution was stirred and cooled to at least 0° C. After adding ethanol absorbing 16% anhydrous ammonia gas, the mixture was stirred for one hour. The solvent was distilled off and the residual crystals were washed with ether to yield 27 g of 4-bromo-3,5-difluorobenzamidine hydrogen chloride.

Step 5:

A sodium ethylate solution was prepared by dissolving 2.8 g of metallic sodium in 220 ml of ethanol. 4 g of 4-bromo-3,5difluorobenzamidine hydrogen chloride and 4.7 g of 3-ethoxy-2pentylacrolein were added to the solution. The method of preparing 3-ethoxy-2-pentylacrolein is described in Chem. Ber. 104, 665–667 (1971). The solution was stirred at a room temperature over night, refluxed for one hour and the ethanol was distilled off. Chloroform was added to the residue, the solution was washed with water and the chloroform was distilled off. The residue was distilled under reduced pressure (bp: 140°−150° C./2 mmHg) and the crystals were treated through a silica gel column using chloroform as the solvent, to yield 0.7 g of 2-(3'-5'-difluoro-4'-bromophenyl)-5-pentylpyrimidine.

Step 6:

0.7 g of 2-(3',5'-difluoro-4'-bromophenyl)-5-pentylpyrimidine, 0.5 g of copper (I) cyanide and 3.5 ml of N-methylpyrrolidone were mixed in a flask and refluxed for 5 hours. The solution was poured into a solution including 1.7 g of iron (III) chloride, 0.4 ml of concentrated hydrochloric acid and 1.7 ml of water. The solution was extracted with chloroform and washed with water and an aqueous 10% solution of potassium hydroxide. The chloroform was distilled off. The residue was treated through a silica gel column using chloroform as the solvent and recrystallized from methanol to yield 0.25 g of 2-(3',5'-difluoro-4'-cyanophenyl)-5-pentylpyrimidine. The crystal—isotropic liquid transfer point (C-I Point) of the compound was 65.3° C.

The following are other examples of the compounds prepared in accordance with the procedures of Example 1:
2-(3',5'-difluoro-4'-cyanophenyl)-5-methylpyrimidine
2-(3',5'-difluoro-4'-cyanophenyl)-5-ethylpyrimidine
2-(3',5'-difluoro-4'-cyanophenyl)-5-propylpyrimidine
2-(3',5'-difluoro-4'-cyanophenyl)-5-butylpyrimidine C-I point : 79.3° C.
2-(3',5'-difluoro-4'-cyanophenyl)-5-hexylpyrimidine
2-(3',5'-difluoro-4'-cyanophenyl)-5-heptylpyrimidine
2-(3',5'-difluoro-4'-cyanophenyl)-5-octylpyrimidine
2-(3',5'-difluoro-4'-cyanophenyl)-5-nonylpyrimidine
2-(3',5'-difluoro-4'-cyanophenyl)-5-decylpyrimidine EXAMPLE 2:
Preparation of 2-(3',5'-difluoro-4'-cyanophenyl)-5-(trans-4'-propylcyclohexyl)pyrimidine.

Steps 1-4:
4-bromo-3,5-difluorobenzamidine hydrogen chloride was prepared as in Steps 1 through 4 of Example 1.

Step 5:
3.7 g of metal sodium was dissolved in 290 ml of ethanol to prepare a sodium ethylate solution. 4 g of 4-bromo-3,5difluorobenzamidine hydrogen chloride and 8 g of 3-ethoxy-2-(trans-4-propylcyclohexyl)-acrolein were added to the solution. The method of preparing 3-ethoxy-2-(trans-4-propylcyclohexyl)-acrolein is described in A. Villiger, Z. Naturforsch 34b, 1535 (1979). The solution was stirred at a room temperature overnight, and refluxed for one hour. The solution was cooled and water was added. The crystals formed were filtered out and recrystallized from a solvent mixture of acetone and methanol, to yield 1.5 g of 2-(3',5'-difluoro-4'-bromophenyl)-5-(trans-4''-propylcyclohexyl)pyrimidine.

Step 6:
1.5 g of 2-(3',5'-difluoro-4'-bromophenyl)-5-(trans-4''-propylcyclohexy)pyrimidine, 0.8 g of copper (I) cyanide and 10 ml of N-methylpyrrolidone were mixed in a flask and refluxed for 5 hours. The solution was poured into a solution including 2.2 g of iron (III) chloride, 0.5 ml of concentrated hydrochloric acid and 2.2 ml of water. The solution was extracted with chloroform, and sequentially washed with water and an aqueous 10% solution of potassium hydroxide. The chloroform was distilled off. The residue was treated through a silica gel column using chloroform as the solvent and recrystallized from a solvent mixture of acetone and methanol, to yield 0.4 g of 2-(3', 5'-difluoro-4 -cyanophenyl)-5-(trans-4''-propylcyclohexyl) -pyrimidine. The C-N point was 114.9° C. and the N-I point was 156.7° C.

The following are other examples of the compounds prepared in accordance with the procedures of Example 2:
2-(3',5'-difluoro-4'-cyanophenyl)-5-(trans-4'''-methylcyclohexyl)-pyrimidine
2-(3',5'-difluoro-4'-cyanophenyl)-5-(trans-4'''-ethylcyclohexyl)-pyrimidine
2-(3',5'-difluoro-4'-cyanophenyl)-5-(trans-4'''-butylcyclohexyl)-pyrimidine
2-(3',5'-difluoro-4'-cyanophenyl)-5-(trans-4'''-pentylcyclohexyl)-pyrimidine
2-(3',5'-difluoro-4'-cyanophenyl)-5-(trans-4'''-hexylcyclohexyl)-pyrimidine
2-(3',5'-difluoro-4'-cyanophenyl)-5-(trans-4'''-heptylcyclohexyl)-pyrimidine
2-(3',5'-difluoro-4'-cyanophenyl)-5-(trans-4'''-octylcyclohexyl)-pyrimidine
2-(3',5'-difluoro-4'-cyanophenyl)-5-(trans-4'''-nonylcyclohexyl)-pyrimidine
2-(3',5'-difluoro-4'-cyanophenyl)-5-(trans-4'''-decylcyclohexyl)-pyrimidine

COMPOSITION EXAMPLE 1

A liquid crystal composition [A] was prepared by mixing 10 wt% 2-(3',5'-difluoro-4'-cyanophenyl)-5-pentyl pyrimidine in a commercially available liquid crystal composition known as ZLI-1565 (manufactured by Merck Inc.). For purpose of comparison, composition [B] was prepared by mixing 10 wt% 2-(4'-cyanophenyl)-5-pentyl pyrimidine in ZLI-1565.

Composition [A]
ZLI-1565 (90 wt %)

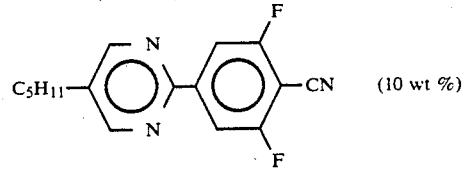

(10 wt %)

Composition [B]
ZLI-1565 (90 wt %)

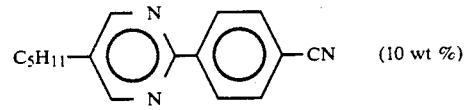

(10 wt %)

The compositions were sealed in 7μm thick twisted nematic liquid crystal cells. The N-I point and voltage-light transmittance under AC static driving at a temperature of 20° C. were measured and the view angle property ($\alpha$) and the threshold property ($\beta$) were determined. The results are shown in Table 1.

TABLE 1

| COMPOSITION | N—I POINT | $V_{10}$ | $\alpha$ | $\beta$ |
|---|---|---|---|---|
| [A] | 67.4° C. | 1.568 | 1.281 | 1.432 |
| [B] | 82.2° C. | 1.984 | 1.281 | 1.422 |

Wherein $V_{10}$ is the voltage at 10% light transmittance of the TN cell measured at an angle in the direction $\theta = 90°$ and $\alpha$ and $\beta$ are calculated using the following equations:

$$\alpha = \theta 90° \ V_{50}/\theta 50° \ V_{50}$$

$$\beta = \theta 90° \ V_{10}/\theta 90° \ V_{90}$$

$\theta 90° \ V_{50}$ and $\theta 50° \ V_{50}$ are the voltage-light transmittance at 50% light transmittance for $\theta = 90°$ and $\theta = 50°$, respectively and $90° \ V_{10}$ and $\theta 90° \ V_{90}$ are the voltage-light transmittance for $\theta = 90°$ at 10 and 90% light transmittance, respectively.

COMPOSITION EXAMPLE 2

A liquid crystal composition [C] was prepared by mixing 10 wt% 2-(3',5'-difluoro-4'-cyanophenyl)-5-(trans-4''-propyl cyclohexyl) pyrimidine in a commercially available liquid crystal composition known as ZLI-1565 (manufactured by Merck Inc.). For purposes of comparison, Composition [B] was prepared by mixing 10 wt% 4-pentyl-4''-cyanoterphenyl in ZLI-1565.

Composition [C]
ZLI-1565 (90 wt %)

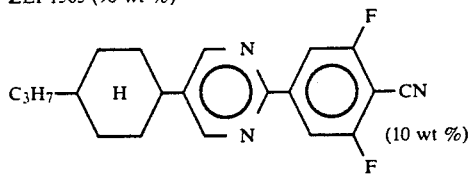
(10 wt %)

Composition [D]
ZLI-1565 (90 wt %)

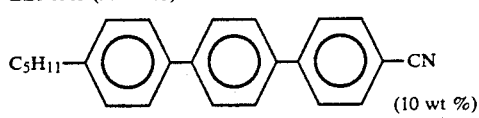
(10 wt %)

The compositions were sealed in 7μm thick twisted nematic liquid crystal cells. The N-I point and voltage-light transmittance under AC static driving at a temperature of 20° C. were measured and α and β were determined. The results are shown in Table 2.

TABLE 2

| COMPOSITION | N—I POINT | $V_{10}$ | α | β |
|---|---|---|---|---|
| [C] | 90.8° C. | 1.835 | 1.292 | 1.402 |
| [D] | 105.5° C. | 2.382 | 1.285 | 1.409 |

In summary, the 2-(3′,5′-difluoro-4′-cyanophenyl) pyrimidine derivatives of the present invention lower the threshold voltage without negatively affecting the view angle property (α) and the threshold property (β).

While the invention has been described in detail with reference to ZLI-1565, it is understood that the decrease in the threshold voltage can be obtained with a wide range of compatible liquid crystal compositions, including:

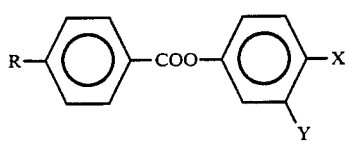

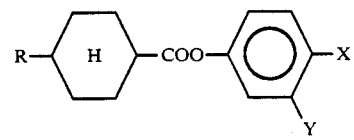

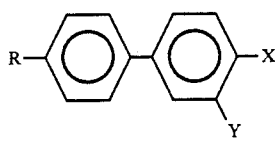

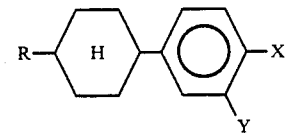

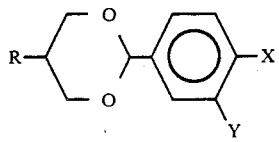

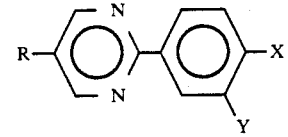

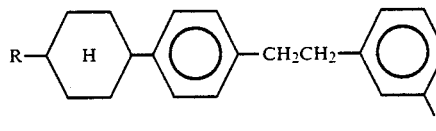

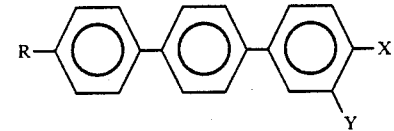

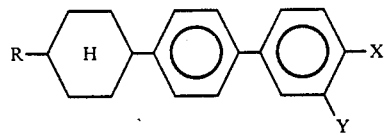

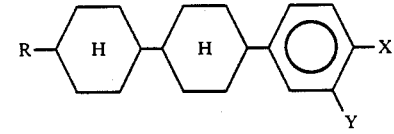

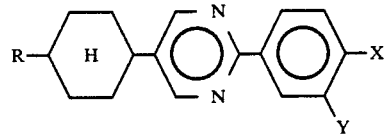

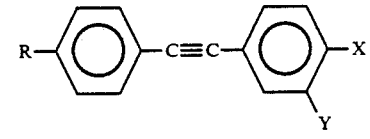

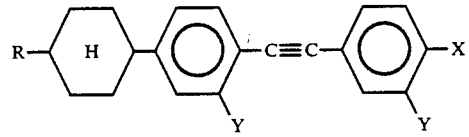

Wherein R is a straight chain alkyl or alkoxy group, X is a straight chain alkyl group, alkoxy group, CN or F, Y is H, F or Cl and n is 0 or 1. Preferably, the pyrimidine derivatives in accordance with the invention are mixed with liquid crystal compounds of the ester and cyclohexylpheny type having the formula:

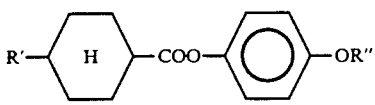

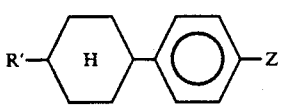

wherein R' and RΔ are alkyl groups and Z is an alkoxy group or CN.

2-(3',5'-difluoro-4'-cyanophenyl) pyrimidine derivatives are included in the composition in at least a minimum effective amount to decrease the threshold voltage as desired up to about 60 weight percent based on the total weight of the composition. Preferably, between about 1 and 30 weight percent is added and most preferably between about 5 and 15 weight percent.

As described above, the 2-(3',5'-difluoro-4'-cyanophenyl) pyrimidine derivatives in accordance with the invention have low threshold voltages. Liquid crystal compositions having low threshold and driving voltages are obtained when the 2-(3',5'-difluoro-4'-cyanophenyl) pyrimidine derivatives of the mixed with conventional liquid crystal compounds. Thus, the pyrimidine derivatives of the invention are extremely useful as constituent components for nematic liquid crystal compositions in super twisted nematic liquid crystal display devices.

It will thus be seen that the objects set forth above, among those made apparent from the preceding description, are efficiently attained and, since certain changes may be made in carrying out the above method and in the composition set forth above without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A 2-(3',5'-difluoro-4'-cyanophenyl) pyrimidine derivative represented by the general formula:

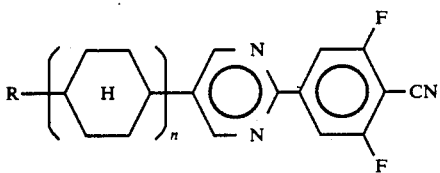

wherein R is a straight chain alkyl group having 1 to 10 carbon atoms: n is 0 or 1 ; and the cyclohexane group is a trans isomer.

2. The 2-(3',5'-difluoro-4'-cyanophenyl) pyrimidine derivative of claim 1, wherein n is 0.

3. The 2-(3',5'-difluoro-4'-cyanophenyl) pyrimidine derivative of claim 1, wherein n is 1.

4. 2-(3',5'-difluoro-4'-cyanophenyl)-5-pentylpyrimidine having the formula:

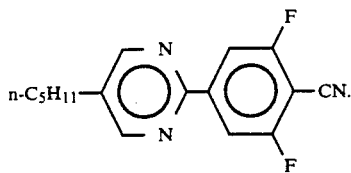

5. 2-(3',5'-difluoro-4'-cyanophenyl)-5-(trans-4''propylcyclohexyl)pyrimidine having the formula:

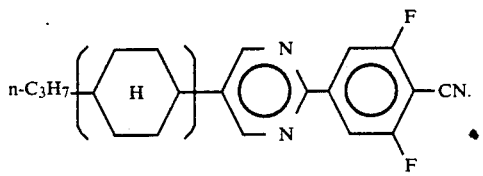

6. The 2-(3',5'-difluoro-4'-cyanophenyl) pyrimidine derivative of claim 1, wherein the number of carbon atoms is R is between about 2 and 5.

7. A liquid crystal composition comprising an effective amount of at least one 2-(3',5'-difluoro-4'-cyanophenyl) pyrimidine derivative for lowering the driving voltage, the pyrimidine derivative having the general formula:

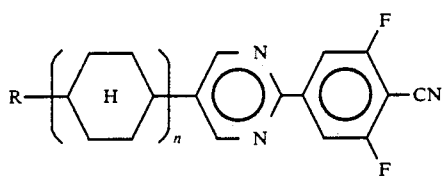

wherein R is a straight chain alkyl group having 1 to 10 carbon atoms; n is 0 or 1; and the cyclohexane group is a trans isomer.

8. The liquid crystal composition of claim 7, wherein the pyrimidine derivative is present between about 1 and 20 weight percent, based on the total weight of the composition.

9. The liquid crystal composition of claim 8, wherein the pyrimidine derivative is present between about 5 and 15 weight percent, based on the total weight of the composition.

10. The liquid crystal composition of claim 7, wherein n is 0.

11. The liquid crystal composition of claim 7, wherein n is 1.

12. The liquid crystal composition of claim 7, wherein the 2-(3',5'-difluoro-4'-cyanophenyl) pyrimidine derivative is 2 (3', 5'-difluoro-4'-cyanophenyl)-5-pentylpyrimidine.

13. The liquid crystal composition of claim 7, wherein the 2-(3',5'-difluoro-4'-cyanophenyl) pyrimidine derivative is 2-(3',5'-difluoro-4'-cyanophenyl)-5-(trans-4'-propylcyclohexyl) pyrimidine.

14. The liquid crystal composition of claim 7, wherein the number of carbon atoms in R is between about 2 and 5.

* * * * *